United States Patent [19]

Garfield et al.

[11] Patent Number: 5,948,762
[45] Date of Patent: Sep. 7, 1999

[54] TREATMENT OF UTERINE CONTRACTILITY DISORDERS WITH A NITRIC OXIDE SYNTHASE SUBSTRATE AND/OR DONOR OR A NITRIC OXIDE INHIBITOR

[75] Inventors: Robert E. Garfield, Friendswood, Tex.; Krzysztof Chwalisz; Radoslaw Bukowski, both of Berlin, Germany; Chandra Yallampalli, Houston, Tex.

[73] Assignees: Schering Aktiengesellschaft, Berlin, Germany; The University of Texas System, Austin, Tex.

[21] Appl. No.: 08/896,017

[22] Filed: Jul. 17, 1997

Related U.S. Application Data

[63] Continuation of application No. 08/152,496, Nov. 16, 1993, abandoned, which is a continuation-in-part of application No. 08/092,426, Jul. 16, 1993.

[51] Int. Cl.$^6$ .......................... A61K 31/04; A61K 31/56; A61K 31/195; A61K 31/155
[52] U.S. Cl. .............................. 514/12; 514/21; 514/171; 514/412; 514/470; 514/561; 514/563; 514/565; 514/648; 514/651; 514/652; 514/742; 514/841; 514/843
[58] Field of Search ................................ 514/12, 21, 561, 514/171, 652, 563, 565, 648, 657, 841, 470, 742, 843, 412

[56] References Cited

U.S. PATENT DOCUMENTS 5,217,997  6/1993  Levere et al. .......................... 514/565
5,508,045  4/1996  Harrison et al. ........................ 424/608

FOREIGN PATENT DOCUMENTS

WO 95/22345  8/1995  WIPO .

OTHER PUBLICATIONS

Yallampalli et al., Soc. Gynecol. Invest. Abst. P41 (1993).
Ramsey et al., Europ. J. of Clinical Investigation, 24:76–78 (1994).
Sladek et al., Endocrinology, 133(4):1899–1904 (1993).
Yallampalli et al., Am. J. Obstet. Gynecol., 169: 1316–1320 (1993).
Yallampalli et al., Am. J. Obstet. Gynecol., 169:1285–1291 (1993).
Yallampalli et al., Am. J. Obstet. Gynecol., 170:175–185 (1993).
Yallampalli et al., Endocrinology, 134(4):1971 (1994).
Greenspoon et al., Lancet, 338:124 (1991).
Izumi et al., Am. J. Obstet. Gynecol., 170:236–245 (1994).
Jennings et al., J. of Mat. Fetal Med., 2:170–175 (1993).
Lees et al., Lancet, 343:1325–1326 (1994).
Natuzzi et al., Biochem. & Biophys. Res. Comm., 194(1):1–8 (1993).
Papka et al., Neuroscience Letters, 147:224–228 (1992).
Bayhi et al., J. Clin. Anesth., 4:487–488 (1992).
Conrad, FASEB, 7:566–571 (1993).
Diamond, J. of Pharm. & Exp. Thera., 168(1):21–30 (1969).
Garfield et al., "Control of Myometrial Contractility and Labor," *Basic Mechanisms Controlling Term and Preterm Labor,* Springer–Verlag Berlin, eds. Chwalisz et al. (1994).

*Primary Examiner*—Herbert J. Lilling
*Attorney, Agent, or Firm*—Millen, White, Zelano, & Branigan, P.C.

[57] ABSTRACT

Dysmenorrhea, disfunctional uterine bleeding, preterm labor and postpartum labor in female mammals are treated by inhibiting uterine contractility by administering thereto a nitric oxide synthase substrate, a nitric oxide donor or both, optionally in combination with one or more of a prostaglandin inhibitor, a prostacyclin-mimetic, a progestin, an oxytocin antagonist or a β-agonist in an amount effective to ameliorate the symptoms thereof; and inadequate menses treated and induction of abortion or stimulation of labor in a pregnant female is achieved by uterine contractility stimulation by administering thereto a nitric oxide inhibitor, either alone or optionally in a combination of progesterone antagonist, an oxytocin or-oxytocin analogue antagonist or a prostaglandin.

10 Claims, 4 Drawing Sheets

TREATMENT OF UTERINE CONTRACTILITY DISORDERS WITH A NITRIC OXIDE SYNTHASE SUBSTRATE AND/OR DONOR OR A NITRIC OXIDE INHIBITOR

CROSS-REFERENCE TO RELATED APPLICATIONS

This application is a continuation, of application Ser. No. 08/152,496, filed Nov. 16, 1993 now abandoned, which is a continuation-in-part of U.S. application Ser. No. 08/092,426, filed Jul. 16, 1993.

BACKGROUND OF THE INVENTION

This invention relates to a method for the treatment of uterine contractility disorders, such as preterm labor, dysmenorrhea and other menstrual problems (e.g., disfunctional uterine bleeding and protracted labor with a nitric oxide synthase substrate (e.g., L-arginine), a nitric oxide donor or both, alone or in further combination with an agent which inhibits uterine contractility (e.g., a prostaglandin inhibitor, progestin, an oxytocin antagonist or β-agonist). Furthermore, this invention relates to a method for the stimulation of uterine contractility for disorders such as inadequate menses, for inducing abortion or for stimulation of labor or to control postpartum hemorrhage, with nitric oxide inhibitors such as L-NAME (NG-nitro-L-arginine methyl ester), alone or in combination with a progesterone antagonist, mimetic, oxytocin and/or prostaglandin.

Uterine contractility disorders are significant health problems. Dysmenorrhea, painful uterine contractions or cramping during the menstrual period, affects almost all gonadal women. Similarly, preterm labor occurs in a significant proportion (about 10%) of pregnant women and is the leading cause of fetal mortality and morbidity. The etiology of uterine contractility disorders and premature labor are largely unknown and effective therapy to inhibit uterine contractility and prevent the symptoms associated with these diseases are unknown. On the other hand, millions of women undergo therapy to stimulate the uterus to contract during pregnancy for abortion, dystocia or as an aid to assist contractility at term, agents such as antiprogestins, oxytocin and prostaglandin analogs are used for these purposes but their effectiveness is not always certain and their mechanism of action is also unknown.

Recently, nitric oxide has been shown to be endothelium derived relaxing factor (EDRF) from the endothelium of blood vessels. Nitric oxide is considered to be a major mediator in the control of vascular reactivity. Nitric oxide is synthesized from the substrate, L-arginine, by nitric oxide synthase located in endothelial cells. Nitric oxide can also be generated by application of various nitric oxide donors such as sodium nitroprusside, nitroglycerin, glyceryl trinitrate, SIN-1, isosorbid mononitrate, isosorbid dinitrate, etc.

Treatment of nonpregnant guinea pigs with L-NAME results in increased uterine contractility. Thus, inhibition of nitric oxide synthase-stimulated uterine contractility indicates that the tonic release of nitric oxide maintains the uterus in a quiescent state. Similarly, treatment of pregnant guinea pig with L-NAME induced preterm labor. On the other hand, treatment of rat uterine strips in vitro pregnant guinea pigs with L-arginine inhibited contractions. These studies show that nitric oxide production by the uterus inhibits contractility and a blockade of this synthesis results in increased muscle contractility both in pregnant and non-pregnant animals. Thus, nitric oxide substrates or donors are useful therapeutically to prevent uterine contractility and nitric oxide inhibitors are effective in stimulating uterine contractions.

Since prostaglandin inhibitors, oxytocin antagonists, β-agonists, and progestins (progesterone) are (or may be) used to inhibit uterine contractions, nitric oxide substrates or donors will be particularly useful in combination with these agents to prevent uterine contractions. Similarly, because progesterone antagonists, prostaglandins, prostacyclin-mimetics, cytokines, and oxytocin are (or may be) used to stimulate uterine contractility, they will be particularly helpful in combination with nitric oxide inhibitors to augment uterine contractility.

EP 0 441 119 A2 discloses the use of L-arginine in the treatment of hypertension and other vascular disorders. It suggests that the mechanism by which L-arginine is effective for this purpose is because it may be the physiological precursor of "the most powerful endothelial-derived releasing factor, nitric oxide." The use of L-arginine in combination with other pharmaceutically active agents is not discussed in this publication. Our previous patent application (Ref: SCH 1237) deals with the treatment of preeclampsia and preterm labor with a combination of a progestational agent and a nitric oxide synthase substrate and/or donor but it does not consider the uses of nitric oxide substrates and/or donor alone for treatment of uterine contractility disorders nor does it consider the inhibition of nitric oxide for the use of stimulating uterine contractions for dystocia, abortion, and the stimulation of labor.

OBJECTS OF THE INVENTION

It is an object of the invention to provide a method for the treatment of uterine contractility disorders with a nitric oxide substrate and/or a donor.

It is another object to provide such a method in combination with prostaglandin inhibitors, prostacyclinmimetics, progestins, oxytocin antagonists, and β-agonists.

It is a further object of this invention to provide a method for the stimulation of uterine contractility to be for the purposes of induction of menses and abortion, or augmentation of labor at term by using nitric oxide inhibitors such as L-NAME.

A further object is to provide a method for the stimulation of uterine contractility (induction of abortion, induction of labor, postpartum hemorrhage) using a nitric oxide inhibitor in combination with a progesterone antagonist, oxytocin and/or prostaglandin.

A further object is the provision of pharmaceutical compositions useful in practicing the methods of this invention.

Upon further study of the specification and appended claims, further objects and advantages of this invention will become apparent to those skilled in the art.

SUMMARY OF THE INVENTION

This invention relates to a method of regulating the nitric oxide dependent contractility of the uterus of a female mammal.

In one aspect, the method comprises administering to a female afflicted with dysmenorrhea, disfunctional uterine bleeding, preterm labor or postpartum hemorrhage to inhibit uterine contractility, a nitric oxide synthase substrate and/or a nitric oxide donor alone or, optionally, in combination with one or more of a prostaglandin inhibitor, a prostacyclin-mimetic, a progestin, an oxytocin-antagonist or a β-agonist, in an amount effective to inhibit uterine contractility and thereby ameliorate the symptoms of the condition to be treated.

In another aspect, the method comprises administering to a female afflicted with inadequate menses or in a pregnant female to induce an abortion or stimulate labor, a nitric oxide inhibitor alone or, optionally, in combination with one or more of a progesterone antagonist, an oxytocin or an oxytocin analogue or a prostaglandin, in an amount effective to stimulate uterine contractility and thereby achieve a normal menses to induce an abortion or stimulate labor, respectively.

DETAILED DISCLOSURE

The method of this invention is useful for treating at least one of dysmenorrhea or other menstrual problem (e.g., disfunctional uterine bleeding) in a nonpregnant female by administering to a non-pregnant gonadal female manifesting the symptoms thereof one or both of a nitric oxide synthase substrate and a nitric oxide donor, alone or in further combination with one or more of a prostaglandin inhibitor (e.g., aspirin, indomethacin), a prostacyclin-mimetic (e.g., iloprost, cicaprost), a progestin, an oxytocin antagonist and a β-agonist, in amounts effective to ameliorate the symptoms thereof, the amount of the progestational agent administered being bioequivalent to 50–300 mg of injected progesterone and the amount of the nitric oxide synthase substrate, nitric oxide donor or both being effective to, respectively, either raise the blood level of circulating L-arginine in a pregnant female to whom the composition is administered to at least about 10–50 mmole above the normally 50–100 mmolar circulating levels or raise nitric oxide donor levels to about 1 to 100 nmolar (nanomolar).

The method of this invention is also useful for treating habitual abortions and preterm labor in a pregnant female by administering to a pregnant female manifesting the symptoms thereof, amounts of at least one of a nitric oxide synthase substrate and a nitric oxide donor effective to inhibit preterm labor, alone or in further combination with one or more of a prostaglandin inhibitor, a progestin, an oxytocin antagonist, a prostacyclin-mimetic and a β-agonist, the amount of the progestational agent administered being bioequivalent to 50–300 mg of injected progesterone and the amount of the nitric oxide synthase substrate, nitric oxide donor or both being effective to, respectively, either raise the blood level of circulating L-arginine in a pregnant female to whom the composition is administered to at least about 10–50 μmol above the normally 50–100 μmol circulating levels, or raise nitric oxide donor levels to about 1 to 100 nmolar.

The method of this invention is also useful for treating inadequate menses in a nonpregnant patient, and for inducing abortion or labor in pregnant patients and for treating postpartum hemorrhage with a nitric oxide inhibitor alone, or in combination with one or more of a progesterone antagonist, oxytocin and/or prostaglandins.

The methods of this invention treat one or more of uterine contractility disorders, such as dysmenorrhea and other menstrual problems (disfunctional uterine bleeding) in a nonpregnant female or preterm labor and protracted labor in a pregnant, preferably human patient, who is manifesting the symptoms thereof or who is a high risk candidate for doing so, e.g., as determined by the progress of a present or previous condition.

Because these abnormal conditions of the nonpregnant state or pregnancy are produced by or aggravated by subnormal nitric oxide synthesis, both nitric oxide synthase substrates, e.g., L-arginine, and nitric oxide donors, e.g., sodium nitro-prusside, nitroglycerin, glyceryl trinitrate, SIN-1, isosorbid mononitrate and isosorbid dinitrate, are useful for ameliorating the symptoms thereof and, in one aspect of the method of this invention, a combination of both are employed. A synergistic effect may be achieved when the nitric oxide substrate and/or donor is used in combinations with one or more of a prostaglandin inhibitor, a progestin, an oxytocin antagonist, and a β-agonist.

Thus, one method aspect of this invention and the pharmaceutical composition aspect of this invention employs (a) either or both of a nitric oxide donor and a nitric oxide substrate and, in addition thereto, optionally (b) one or more of a prostaglandin inhibitor (e.g., aspirin, indomethacin, or ibubrophen), a progestin (progesterone, hydroxyprogesterone caproate, norgestrel, medroxyprogesterone acetate, gestodene, etc.), an oxytocin antagonist, and a β-agonist (e.g., fenoterol, ritodrin, salbutinol, terbutaline, etc.).

Examples of dosage ranges of typical NO-substrates and NO-donors (per os) are:

|  | total dose: |
|---|---|
| L-Arginine | 500 mg–10 g p.o. |
| Sodium Nitroprusside | range 500–2000 ug/kg/day |
| Nitroglycerin | 0.5–10 mg |
| Isosorbid mononitrate | 10–100 mg |
| Isosorbid dinitrate | 10–100 mg |

The following are typical oral dosage ranges active agents of the progestin and the optional other active agents concurrently administered with the nitric oxide substrate or donor:

Progestins A daily dose bioequivalent to 50–300 mg of progesterone/day, e.g., an injectable suspension of medroxyprogesterone acetate to provide a weekly dose of thereof of 100–1000 mg. or tablets or dragees providing an oral dose thereof of 5–10 mg/day; an injectable solution of hydroxyprogesterone caproate which provides a weekly dose of 250–500 mg; tablets, capsules or dragees of northindrone acetate which provide a daily dose of 5–20 mg.

The second method of this invention employs treatment of inadequate menses in a nonpregnant female, termination of pregnancy (as an abortifacient), and stimulation of labor during normal child birth in a pregnant, preferably human female, who is manifesting the symptoms thereof or who is a high risk candidate for doing so, e.g., as determined by the progress of a present or previous condition.

Because these symptoms are produced by elevated levels of nitric oxide, nitric oxide inhibitors, e.g., L-NAME, L-NIO, L-NA, etc. are useful for ameliorating the symptoms thereof, and in one aspect of this invention, a combination thereof is employed. Furthermore, a synergistic effect may be achieved when a nitric oxide inhibitor is used in combination with one or more of an antiprogestin (e.g., RU 486 [mifepristone], onapristone), oxytocin (e.g., Syntocinon), and prostaglandins (e.g., sulprostone, PGE2, etc.)

Therefore, the second method aspect of this invention and the pharmaceutical composition aspect of this invention employs (a) a nitric oxide inhibitor alone and, optionally (b) in addition thereto, one or more of a progesterone antagonist, a cytokine, an oxytocin agonist, and a prostaglandin.

The dosage range of typical nitric oxide inhibitors, e.g., L-NAME, N-NA and N-NIO (per os), is 0.1 to 10 g/day.

The following are the typical oral dose ranges of the antiprogestins and other optional active agents used concurrently with the nitric oxide inhibitors:

| | |
|---|---|
| RU 486 | 10–600 mg/day |
| Onapristone | 10–600 mg/day |

| | |
|---|---|
| Sulprostone | 100–2000 µg/day i.m. or i.v. |
| Gemeprost | 0.5–5 mg/day intravaginally |
| Misoprostol: | 50–5000 µg/day orally |
| PGE2 | 0.1–5 µg/min i.v. |
| | 100–1000 µg intravaginal gel |
| PGF2a | 0.1–200 µg/min i.v. |

| | |
|---|---|
| Syntocinon | 0.5–20 mIU/min i.v. |

| | |
|---|---|
| Fenoterol (Partusisten ®) | 0.5–3.0 µg/min i.v.; 20–200 mg/day orally |
| Ritodrin (Pre-par ®) | 20–200 mg/day oral |

Magnesium salts a) 1.0 to 20.0 mmol magnesium as a 10 to 20% aqueous solution of: $MgSO_4$, $MgSO_4.7H_2O$, Mg-L-apartate.$HCl.3H_2O$, Mg-ascorbate, Mg-salt of levulinic acid; administration is i.m. or i.v.

b) 1.0 to 20.0 mmol magnesium in form of a tablet, film tablet, capsule, soluble powder or chewable tablet: $MgHPO_4.3H_2O$, Mg-citrate.$3H_2O$, $MgCO_4$, Mg-D,L-hydrogenaspartate.$HCl.3H_2O$, Mg-L-hydrogenaspartate, Mg-L-hydrogenglutamate, Mg-ascorbate, MgO.

The pharmacologically active agents employed in this invention can be administered in admixture with conventional excipients, i.e., pharmaceutically acceptable liquid, semi-liquid or solid organic or inorganic carriers suitable, e.g., for parental or enteral application and which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring, and/or aromatic substances and the like which do not deleteriously react with the active compounds.

For parental application, particularly suitable are solutions, preferably oily or aqueous solutions, as well as suspensions, emulsions, or implants, including suppositories. Ampoules are convenient unit dosages.

In a preferred aspect, the composition of this invention is adapted for ingestion.

For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein the active compound is protected with differentially degradable coatings, e.g., by microencapsulation, multiple coatings, etc.

Suitable for oral administration are, inter alia, tablets, dragees, capsules, pills, granules, suspensions and solutions.

Each unit dose, e.g., each tablespoon of liquid or each tablet, or dragee contains, for example, 5–5000 mg of each active agent.

Solutions for parental administration contain, for example, 0.01–1% of each active agent in an aqueous or alcoholic solution.

The nitric oxide substrate and/or donor can be administered as an admixture with the progestational agent and other optional active agent or as a separate unit dosage form, either simultaneously therewith or at different times during the day from each other.

The combination of active agents is preferable administered at least once daily (unless administered in a dosage form which delivers the active agents continuously) and more preferable several times daily, e.g., in 2 to 6 divided doses. The typical dose is about 0.5 to 1000 mg of each active agent, although some less active agents, e.g., L-Arginine, require much higher oral dosages, e.g., 500 to 10,000 mg, and others, e.g., sodium nitroprusside, require lower doses, e.g., 500–2,000 µg/kg/day. Doses for nitroglycerin typically are: orally 2.5 mg 2×daily; sublingually, 0.8 mg 1–4×daily; and transdermally, 0.2–0.4 mg/hr. Since the $LD_{50}$ dosages of most of these active agents is known in the prior art, a lower dosage regimen can be initiated and the dosage increased until a positive effect is achieved or a higher dosage regimen can initially be employed, e.g., in a crisis situation, and the dosages regulated downward as relief from the symptoms is achieved.

In humans, both L-arginine and progesterone (or bioequivalent of another progestin) should be given in a ratio which produces blood plasma levels of about 1–5 mMol/ml and 300–1,000 ng/ml (0.9–3 µMol/l), respectively. The NO-donor, e.g., sodium nitroprusside, should be given with the progesterone (or bioequivalent of another progestin) in a ratio producing blood plasma levels of about 1–10 µMol/l and 300–100 ng/ml (0.9 µMol/l), respectively.

BRIEF DESCRIPTION OF THE DRAWINGS

Various other objects, features and atten4dant advantages of the present invention will be more fully appreciated as the same becomes better understood when considered in conjunction with the accompanying drawings, wherein.

DISCUSSION OF THE DRAWINGS

Figure 1:
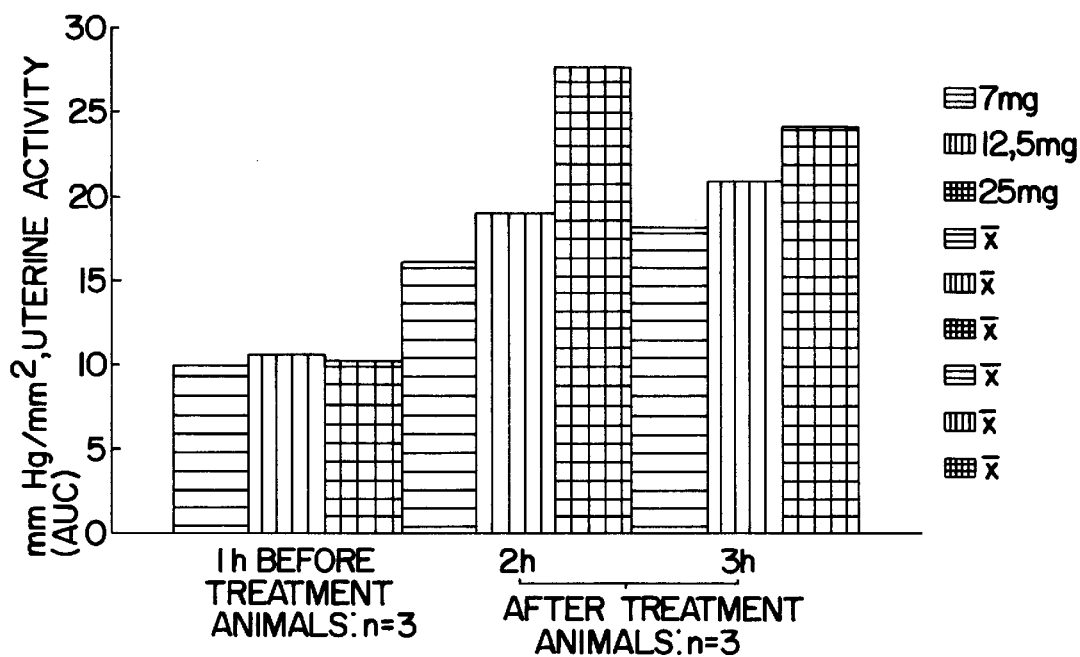
FIG. 1 is the result of recording uterine activity (area under the curve [AUC] of the uterine pressure mmHg/mm2 per unit time) 1 hour before and following L-NAME treatment (7, 12,5 and 25 mg s.c.) at 2 and 3 hours in nonpregnant guinea pigs (n=3/group)

The bar graphs in FIG. 1 show that treatment of nonpregnant guinea pigs with L-NAME (7, 12.5 and 25 mg s.c.)

increased uterine contractility and pressure in a dose- and time-dependent fashion. The uterine pressure after 2 and 3 hours treatment with L-NAME was approximately double (ca. 10 mm Hg/mm$^2$) that of the control recording prior to treatment (ca. 10 mmg Hg).

The data show a time and dose-dependent effect of L-NAME to increase in FIG. 1 uterine activity. From a basal level of uterine activity of about 10 mg Hg/mm2, uterine activity approximately doubled after L-NAME treatment at 2 and 3 hours with both 7 and 12.5 mg and tripled after 25 mg.

Figure 2:
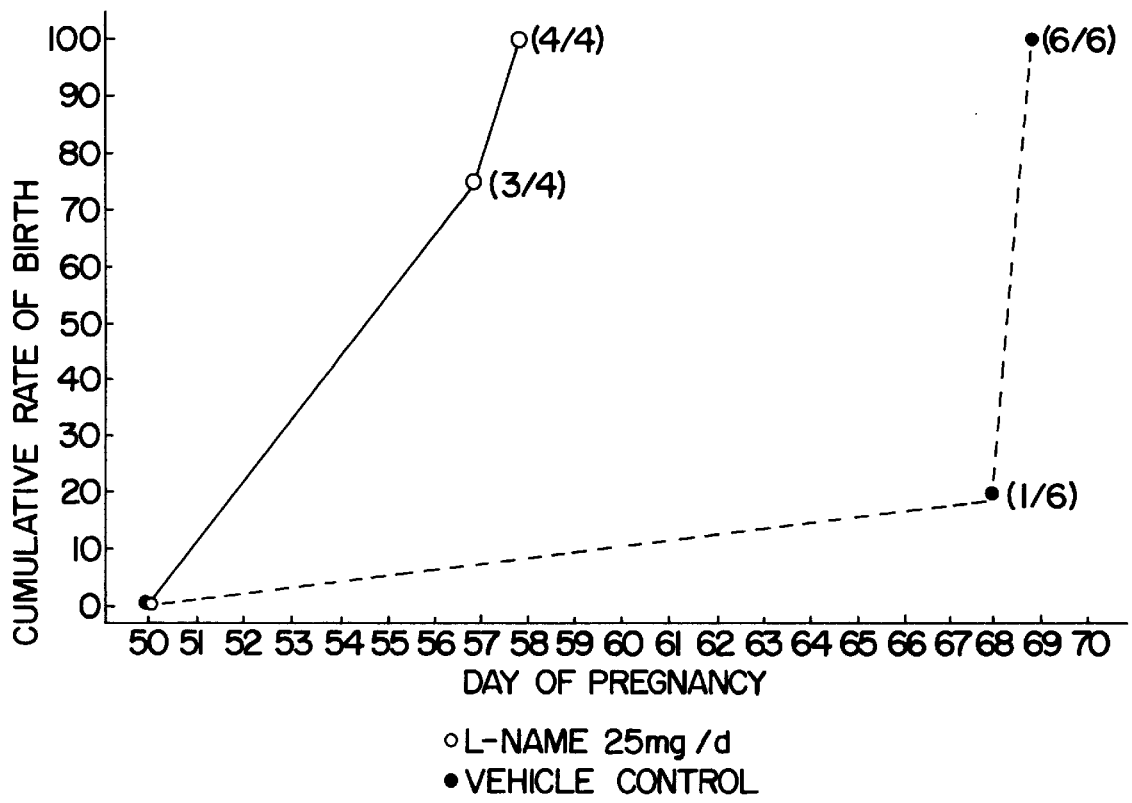
FIG. 2 shows the effects of L-NAME at 25 mg/day/animal to induce birth in preterm-guinea pigs (day 50–57 of pregnancy)

In experiments with pregnant guinea pigs, s.c. infusion of L-NAME (25 mg/day) starting on day 50 of pregnancy resulted in preterm birth (FIG. 2).

Figure 3:
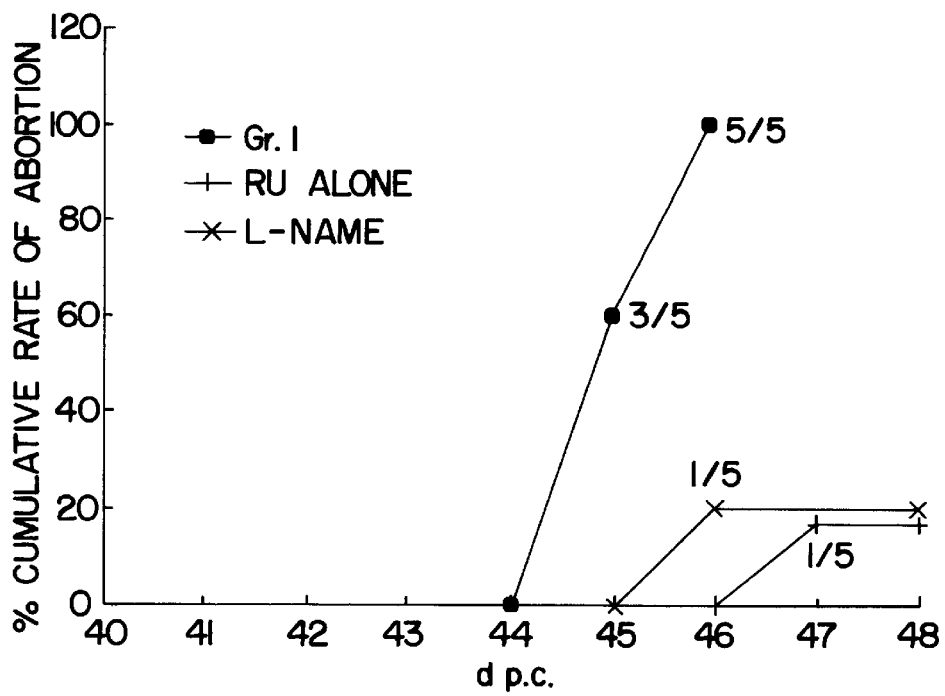
FIG. 3 shows the synergistic effect of L-NAME (25 mg/day/animal day 40–47 of pregnancy) with mifepristone (RU 486; 10 mg/animal s.c. day ) in inducing abortion in mid-pregnant guinea pigs (day 40–47 of pregnancy)

FIG. 3 shows a synergistic effect of L-NAME in combination with RU 486 in inducing abortion in mid-pregnant guinea pigs. At this stage of pregnancy both 25 mg/day/animal L-NAME and 10 mg RU 486 (controls) do not induce abortion alone. A combination of both compounds very effectively induced abortion within two days in all animals.

The strip chart recordings. of FIG. 4 show that the application of L-arginine (1–3 nM) (A, B, E), sodium nitroprusside (5 nM) (C), nitric oxide (0.1 nM) (D) to muscle baths produced substantial relaxations. The effects of L-arginine were reversed by L-NAME (3 nM) (B) and methylene blue (0.1 nM) (E). These are typical recordings of 8–16 strips from 6 animals in each group. Each upstroke from baseline represents a contraction.

The strip chart recording of FIG. 4 show that the application of sodium nitroprusside (SNP) caused sustained relaxation in spontaneously contracting uterine strips after a lag period and that tissues in the relaxed state were responsive to potassium chloride. Similar recordings of 12 uterine strips from 4 animals were obtained.

Figure 4A:
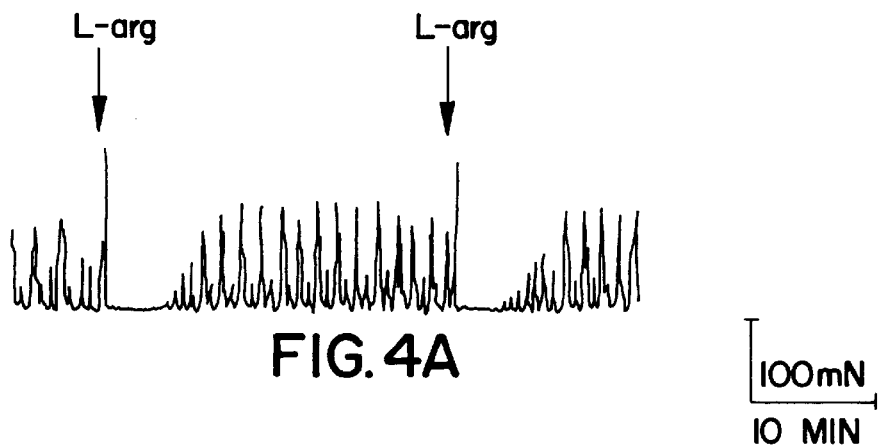
FIGS. 4A–4E show the effect of L-arginine and L-NAME on spontaneously contracting uterine strips from rat uterus obtained on day 18 of pregnancy.
Figure 4B:
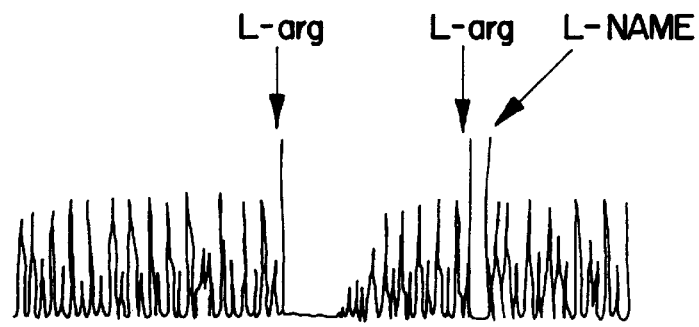
Figure 4C:
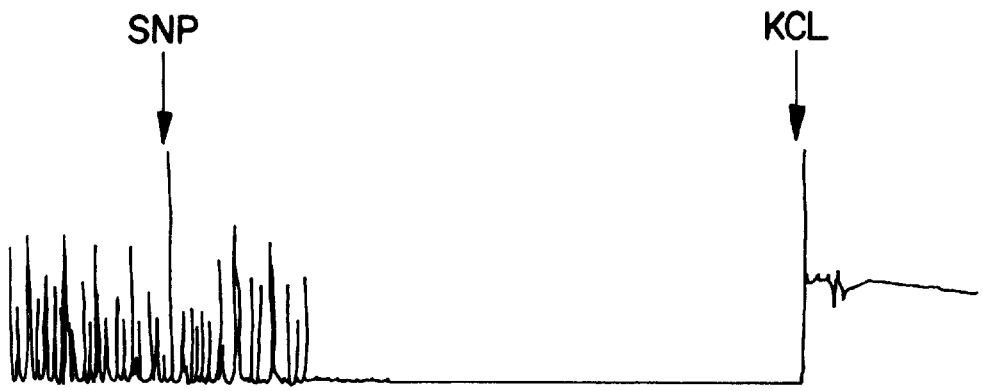
Figure 4D:
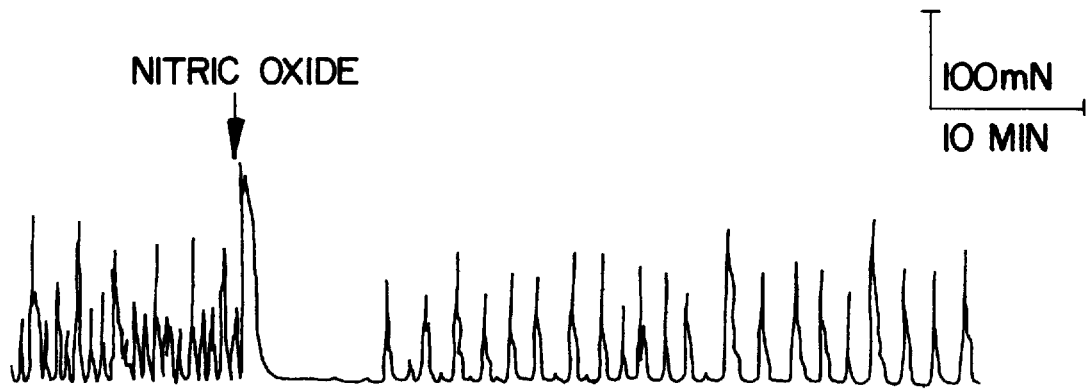
Figure 4E:
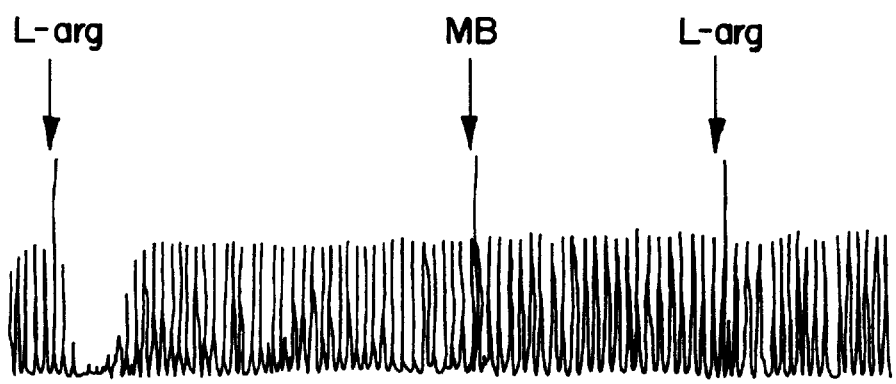

The strip chart recording in FIG. 4D show the relaxation produced by authentic nitric oxide gas (0.1 nM). Similar recordings were obtained from 8 strips from 4 animals.

The strip chart recordings of FIG. 4 show that L-arginine (1 nM) produced relaxation of spontaneously contracting tissues and these effects were repeatable in the same strip (as in FIG. 4A) and that the relaxation effect of L-arginine (1 nM) was abolished by methylene blue (0.1 nM) when added before the application of L-arginine (B).

Application of L-arginine (3 nM) to the muscle bath caused immediate relaxation (10–15 min duration) of contractility (A). The effect of L-arginine (3 nM) was antagonized by L-NAME (3 nM) when added during an L-arginine-induced relaxation (B). These are typical recordings and each of the upstroke from base line represents a contraction. Similar responses were observed in 12 uterine strips from 6 animals. Sodium nitroprusside (SNP), a nitric oxide donor, caused relaxation of spontaneously contracting pregnant rat uterus on day 18 of gestation. Application of sodium nitroprusside caused sustained relaxation in spontaneously contracting uterine strips after a lag period (C). Tissues in the relaxed state after nitroprusside were responsive to potassium chloride (KCI) (D).

The effect of methylene blue on the L-arginine-induced relaxation of uterine strips from pregnant rats on day 18 of gestation (i.e. shown in E). L-arginine (1 nM) produced relaxation of spontaneously contracting tissues and the relaxation effect of L-arginine (1 nM) was abolished by methylene blue (0.1 nM) when added before the application of L-arginine (E).

Figure 5:
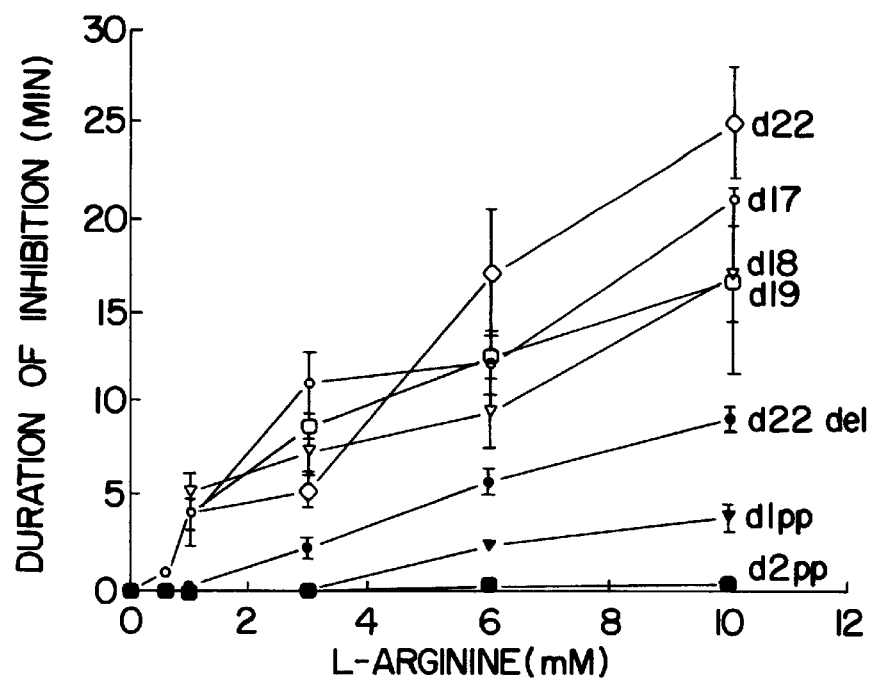
FIG. 5 shows the dose-dependent relaxation effects of L-arginine (0.1 nM to 10 nM) on spontaneously contracting uterine strips from rats at different stages of gestation, during delivery and postpartum.

In the experiments whose results are shown by the graph of FIG. 5, the tissues were obtained on days 17–22 (d17, d18, d19 and d22) of gestation, on day 22 before delivery and during spontaneous delivery (d22 DEL, 1–3 pups delivered), or on 1 (d1pp) and 2 (d2pp) days postpartum. The duration of complete inhibition of spontaneous uterine contractions are dose-dependent. The effects of L-arginine from concentrations of 1 nM are significantly (P<0.01) decreased during spontaneous delivery at term and postpartum, compared to all other times. Each data point represents mean±S.E.M. The total number of strips studied at each time period was 8–16 from 4–6 animals per groups.

Figure 6:
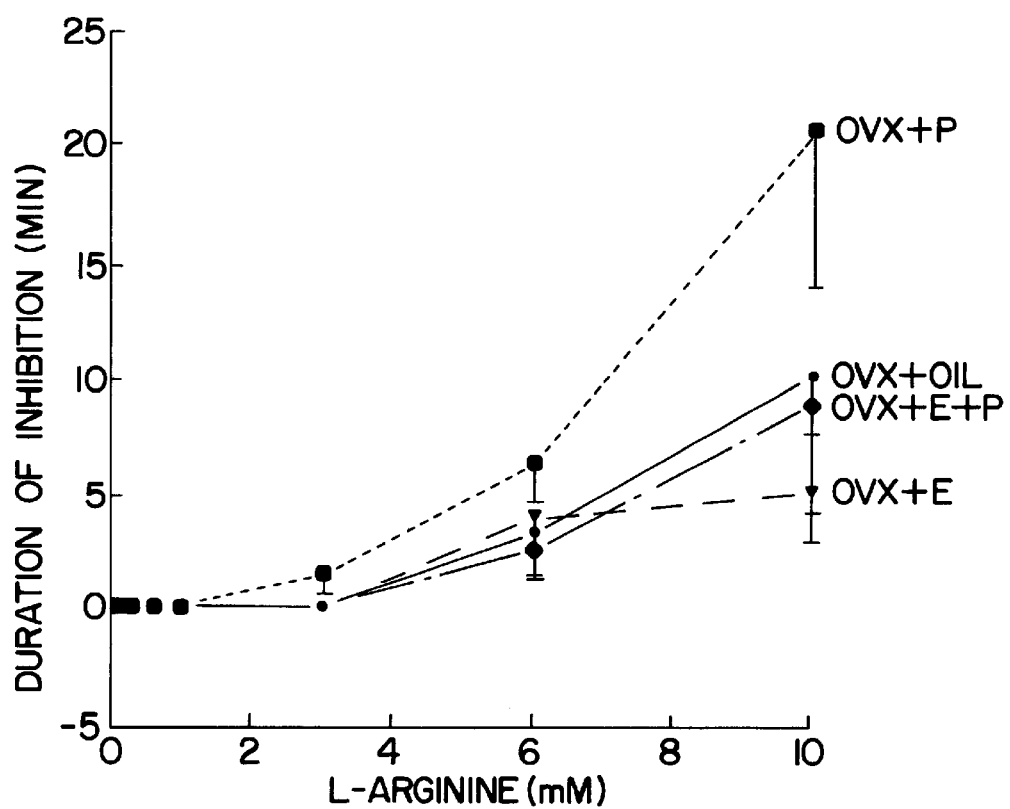
FIG. 6 shows dose response effects of L-arginine (0.6 nM to 10 nM) on the spontaneous contractility of uterine strips from ovariectomized nonpregnant adult rats.

In experiments whose results are shown by the graph of FIG. 6, nonpregnant ovariectomized rats received s.c. injection of 1 μg estradiol-17β (OVX+E), 2 mg progesterone (OVX+P, estradiol and progesterone (OVX+E+P) in sesame oil or oil alone (OVX+oil) for 3 days prior to contractility measurements. Values are mean±S.E.M. for 4 strips from each animal from 4 rats per group. Data are analyzed by repeated measures ANOVA on four groups. P<0.05 OVX+P vs OVX+E.

It can be concluded from these studies that the inhibition of nitric oxide synthesis with L-NAME results in an increase in uterine contractility and intrauterine pressure in both nonpregnant and pregnant guinea pigs. These results indicate that nitric oxide must be produced by the uterus to maintain the organ in a state of quiescence. Furthermore, the application of L-NAME to pregnant guinea pigs results in preterm labor and birth. This data shows that nitric oxide is required for maintaining of a pregnancy and that when the synthesis of nitric oxide is blocked labor ensues.

The results of these studies also indicate that nitric oxide substrate (L-arginine) treatment of contracting pregnant and nonpregnant rat uterine strips in vitro substantially inhibit contractility. Similar effects are demonstrated with authentic nitric oxide gas and nitric donors (sodium nitroprusside). Further, the uterine relaxation effect of nitric oxide substrate is blocked by methylene blue (an inhibitor of guanylate cyclase). These studies clearly show that an L-arginine—nitric oxide—CGMP system exists in the uterus and that this system controls uterine contractility both in the pregnant and nonpregnant states.

Additionally, the ability of L-arginine to inhibit contractility is reduced during labor and delivery. Also, progesterone controls the inhibitory response to L-arginine. Therefore, these studies demonstrate that nitric oxide can maintain uterine quiescence during pregnancy but not during delivery. Furthermore, nitric oxide synthesis is regulated by progesterone (upregulated). Thus, a decrease in progesterone at term inhibits nitric oxide production and thus can initiate labor.

From these original studies it can be seen that nitric oxide substrates and donors are useful to inhibit uterine contractility and the inhibition of nitric oxide synthesis or effects is useful to stimulate uterine contractility. Furthermore, since progesterone is necessary for the effectiveness of nitric oxide, a progestin in combination with a nitric oxide substrate and/or donor is a useful combination for inhibition, whereas the combination of an antiprogestin with a nitric oxide inhibitor is effective to stimulate uterine contractility.

In addition, since other treatments are used to inhibit or stimulate uterine contractility and labor, the above regimes are efficacious with combinations of prostaglandin inhibitors, oxytocin antagonists, prostacyclin mimetics and β-agonists with a nitric oxide substrate and/or a donor to inhibit uterine contractility. Conversely, combinations of antiprogestins, prostaglandins and cytokines with nitric oxide inhibitors are useful to stimulate uterine contractility.

Thus, the method of this invention relates to the treatment of uterine contractility disorders, such as preterm labor, postpartum hemorrhage, dysmenorrhea and other menstrual problems (e.g., disfunctional uterine bleeding), and protracted labor with.a nitric oxide synthase substrate (e.g., L-arginine), a nitric oxide donor or both, alone or in further combination with agents which inhibit uterine contractility (e.g., prostaglandin inhibitors, prostacyclin-mimetics, progesterone, oxytocin antagonists and β-antagonists). Furthermore, this invention relates to a method for the stimulation of uterine contractility for disorders such as inadequate menses, induction of an abortion and stimulation of labor with nitric oxide inhibitors such as L-NAME (NG-nitro-L-arginine methyl ester) alone or in combination with a progesterone antagonist, oxytocin and/or a prostaglandin.

The method of treatment described in this invention can also be employed for the treatment of other smooth muscle disorders such as those involving the cardiovascular system, gastrointestinal tract, airways, urinary tract (e.g., urinary incontinence) etc. The method can also be employed for the treatment of hypertension (in both males and females) and thrombotic disorders, following the dosage regimes described herein.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever. The entire disclosure of all applications, patents and publications, cited above and below are hereby incorporated by reference.

EXAMPLES

Examples of Uterine Contractility Inhibition

Example 1—Treatment of Dysmenorrhea

To a human, nonpregnant cycling female (ca. 20 to 45 years; 50–80 kg) displaying the symptoms of dysmenorrhea, administer 0.5 to 20 g of L-arginine per os daily in three divided doses until the symptoms are ameliorated. Thereafter, administer 5 to 20 g of L-arginine daily until remission of symptoms again occurs.

Example 2—Treatment of Dysmenorrhea

To a human female comparable to and displaying the same symptoms as the one described in Example 1, administer daily 2×2.5 mg of nitroglycerine following the same protocol, until the symptoms are ameliorated.

Example 3—Treatment of Dysmenorrhea

To a human female comparable to example 1, administer 0.5 to 20 g of L-arginine daily, and/or 2×2.4 mg of nitroglycerine in combination with 60 mg of progesterone daily to ameliorate the symptoms.

Example 4—Treatment of Dysmenorrhea

To a human female comparable to example 3 administer 0.5 to 20 g of L-arginine daily, and/or nitroglycerin 2×2.5 g in combination with a prostaglandin inhibitor (e.g., aspirin 500 mg 4× daily).

Example 5—Treatment of Preterm Labor

To a pregnant human female (ca. 20–40 years, 50–80 kg) usually in her second half of pregnancy and displaying signs or preterm labor, including premature labor contractions administer 0.5 to 20 g of L-arginine daily in three divided doses until the symptoms are ameliorated.

Example 6—Preterm Labor

To a pregnant human female comparable to the one described in Example 5, administer daily 2×25 mg of nitroglycerine until the symptoms are relieved.

Example 7—Preterm Labor

To a pregnant human female comparable to the one described in Example 5 administer daily 0.5 to 20 g of L-arginine, and/or nitroglycerine 2××25 mg in combination with aspirin 100–2000 mg daily until remission of the symptoms occur.

Example 8—Preterm Labor

To a pregnant human female comparable to the one described in Example 5 administer daily L-arginine 0.5 to 20 g and/or nitroglycerine 2×25 mg in combination with fenoterol 20–200 mg daily orally to relieve the symptoms.

Examples of Labor Stimulation

Example 8—Stimulation of Labor

To a pregnant female (ca. 20–40 years; 60–80 kg) at term (39–41 wks) displaying signs of weak labor contractions and cervical incompetence, and not advancing in the parturition process, administer L-NAME (0.1 to 10 mg/kg) daily in divided in doses per os to ameliorate the symptoms and stimulate labor.

Example 9—Stimulation of Labor

To a pregnant female patient comparable to Example 8, administer L-NAME 0.1 to 10 mg/Kg daily with an anti-progestin (e.g., mifepristone [RU 486], 100–600 mg/day for 2 or 3 days) to relieve the symptoms.

Example 10—Stimulation of Labor

To a pregnant female patient comparable to Example 8, administer daily 0.1—10 mg/kg of L-NAME with a prostaglandin (e.g., PGE2 0.1–5 μg/min i.v.) to ameliorate the symptoms.

Example 11—Stimulation of Labor

To a pregnant female comparable to Example 8, administer daily 0.1 to 10 mg/kg of L-NAME with an oxytocin (e.g., syntocinon 0.5–20 mIU/min i.v.).

Example 12—Abortion and Termination of Pregnancy

To a pregnant female (ca. 20–40 years; 60–80 kg) in her first trimester (1 to 12 wks of gestation) wishing to terminate her pregnancy, administer L-NAME 0.1 to 10 mg/kg daily, to induce uterine contractility and end the pregnancy.

Example 13—Abortion and Termination of Pregnancy

To a pregnant female patient comparable to Example 12, administer L-NAME 0.1 to 10 mg/kg daily with a progesterone antagonist (e.g., RU 486 100–600 mg/day orally).

Example 14—Abortion and Termination of Pregnancy

To a pregnant female human similar to Example 12, administer L-NAME 0.1 to 10 mg/kg daily with a prostaglandin (e.g., sulprostone 100–2000 μg/day i.v. or i.m.) to terminate the pregnancy.

Example 15—Treatment of Inadequate Menses

To a nonpregnant human female (ca. 20 to 40 years; 50 to 80 kg) displaying problems with inadequate menses during the cycle, administer L-NAME 0.1 to 10 mg daily alone or in combination with an antiprogestin (e.g., RU 486 100–600 mg/day orally) and/or a prostaglandin (e.g., sulprostone 100–2000 μg/day i.v. or i.m. or misoprostol.50–5000 μg/day mg orally).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of regulating the nitric oxide dependent contractility of the uterus of a non-pregnant female mammal, comprising administering a nitric oxide inhibitor in an amount effective to stimulate uterine contractility.

2. A method of claim 1 for regulating the nitric oxide dependent contractility of the uterus of a non-pregnant female mammal, which comprises administering to a nonpregnant female suffering from inadequate menses an effective amount of a nitric oxide inhibitor alone or, optionally, in combination with an effective amount of one or more of a progesterone antagonist, an oxytocin or an oxytocin analogue or a prostaglandin, in an amount effective to stimulate uterine contractility and thereby achieve a normal menses.

3. The method of claim 2, wherein the female mammal is a human.

4. The method of claim 3, wherein NG-nitro-L-arginine methyl ester ("L-NAME") or equivalent nitric oxide inhibitor is administered.

5. The method of claim 3, wherein L-NAME in combination with an effective amount of a progesterone antagonist is administered.

6. The method of claim 5, wherein the progesterone antagonist is mifepristone.

7. The method of claim 3, wherein L-NAME is administered in combination with a prostaglandin.

8. The method of claim 7, wherein the prostaglandin is sulprostone.

9. The method of claim 3, wherein L-NAME is administered in combination with an oxytocin antagonist.

10. A method of stimulating the nitric oxide dependent contractility of the uterus of a non-pregnant female mammal comprising administering a nitric oxide inhibitor in an amount effective to stimulate uterine contractility.

* * * * *